US011016071B2

(12) United States Patent
Druon et al.

(10) Patent No.: US 11,016,071 B2
(45) Date of Patent: May 25, 2021

(54) MICROALGAL FLOUR COMPOSITIONS OF OPTIMISED SENSORY QUALITY

(71) Applicant: Corbion Biotech, Inc., South San Francisco, CA (US)

(72) Inventors: Amandine Druon, Lille (FR); Heike Jerosch, Estaires (FR); Marilynne Guillemant, Aire sur la Lys (FR); Samuel Patinier, Quesnoy-sur-Deule (FR)

(73) Assignee: Corbion Biotech, Inc., South San Francisco, CA (US)

( * ) Notice: Subject to any disclaimer, the term of this patent is extended or adjusted under 35 U.S.C. 154(b) by 234 days.

(21) Appl. No.: 15/926,899

(22) Filed: Mar. 20, 2018

(65) Prior Publication Data

US 2018/0224417 A1   Aug. 9, 2018

Related U.S. Application Data

(63) Continuation of application No. 14/900,654, filed as application No. PCT/FR2014/051589 on Jun. 25, 2014, now abandoned.

(30) Foreign Application Priority Data

Jun. 26, 2013 (FR) ...................... 1356113

(51) Int. Cl.
*G01N 33/10* (2006.01)
*A23L 17/60* (2016.01)
*G01N 30/72* (2006.01)
*G01N 33/00* (2006.01)
*G01N 33/04* (2006.01)
*A23C 9/13* (2006.01)

(52) U.S. Cl.
CPC .............. *G01N 33/10* (2013.01); *A23C 9/13* (2013.01); *A23C 9/1315* (2013.01); *A23L 17/60* (2016.08); *G01N 30/7206* (2013.01); *G01N 33/0001* (2013.01); *G01N 33/04* (2013.01); *A23V 2002/00* (2013.01)

(58) Field of Classification Search
CPC ......... G01N 30/10; A23L 7/60; A23C 9/1315; A23V 2002/00
See application file for complete search history.

(56) References Cited

U.S. PATENT DOCUMENTS

| | | | |
|---|---|---|---|
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |
| 2010/0303957 A1 | 12/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2012/0128851 A1 | 5/2012 | Brooks et al. | |
| 2012/0294913 A1* | 11/2012 | Asano ............. | A61K 8/022 424/401 |
| 2013/0122180 A1 | 5/2013 | Brooks et al. | |
| 2016/0143336 A1 | 5/2016 | Druon et al. | |
| 2016/0192691 A1 | 7/2016 | Druon et al. | |

FOREIGN PATENT DOCUMENTS

| | | |
|---|---|---|
| JP | 2001-095481 | 4/2001 |
| JP | 2001-095481 A | 4/2001 |
| WO | WO 2010/045368 A2 | 4/2010 |
| WO | WO 2010/120923 A1 | 10/2010 |
| WO | WO 2011/130578 A2 | 10/2011 |
| WO | WO 2014/117163 A1 | 7/2014 |

OTHER PUBLICATIONS

Callejon, R. M., et al., "Volatile and sensory profile of organic red wines produced by different selected autochthonous and commercial *Saccharomyces cerevisiae* strains,"*Analylica Chimica Acta*, 2010, vol. 660, pp. 68-75.
Cha, Y. J. el al. "Volatile components in salt-fermented fish and shrimp pastes." Journal of Food Science (1995) 60: 19-24. (Year 1995).
Crisosto, C.H., et al. , "Segregation of peach and nectarine (*Prunus persica* (L.) Batsch) cultivars according to their Organoleptic characteristics," *Postharvest Biology and Technology*, 2006, vol. 29, pp. 10-18.
Das, R., et al. , "Development of Electronic Nose Method for Evaluation of HDPE Flavour Characteristics, Correlated with Organoleptic Testing ," *Packaging Technology and Science*, 2007, vol. 20, pp. 125-136.
Dupuy, H.P. et al., "Direct sampling capillary gas chromatography of volatiles in vegetable oils." JAOCS (185) 62: 1690-1693 (Year 1985).
Guil-Guerrer, J. L., et al., "Functional properties of the biomass of three microalgal species", *Journal of Food Engineering*, Dec. 1, 2004, vol. 65, No. 4, pp. 511-517.
Santos, J.E. R., et al. , "Analysis of Volatile Organic Compounds in Virgin Coconut Oil and their Sensory Attributes ," *Philippine Journal of Science*, Dec. 2011 , vol. 140, No. 2, pp. 161-171.
Yamaguchi, Kenji et al., "Volatile constitunets of green tea, gyokuro." J. Agric. Food Chem. (1981) 29: 366-370 (Year 1981).

(Continued)

*Primary Examiner* — Christopher Adam Hixson
(74) *Attorney, Agent, or Firm* — Leydig, Voit & Mayer, Ltd.

(57) ABSTRACT

Thus, the present invention relates to a method for determining the organoleptic quality of a microalgal flour composition, comprising determining the total content of 13 volatile organic compounds, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

19 Claims, 3 Drawing Sheets

(56) References Cited

OTHER PUBLICATIONS

Written Opinion of the Searching Authority for International Patent Application No. PCT/FR2014/051589, dated Oct. 6, 2014, pp. 1-10.
Chacón-Lee et al., "Microalgae for "Healthy" Foods—Possibilities and Challenges," Comp. Rev. Food Sci. and Safety, 9: 655-675 (2010).
"Enter the World of Microalgae," Roquette (Jun. 2014).
International Bureau, International Preliminary Report on Patentability in International Application No. PCT/FR2014/051589, dated Dec. 29, 2015.
International Bureau, International Search Report in International Application No. PCT/FR2014/051589, dated Oct. 6, 2014.

\* cited by examiner

MICROALGAL FLOUR COMPOSITIONS OF OPTIMISED SENSORY QUALITY

CROSS-REFERENCE TO RELATED APPLICATIONS

This application is a continuation of U.S. patent application Ser. No. 14/900,654, filed Dec. 22, 2015, entitled "MICROALGAL FLOUR COMPOSITIONS OF OPTIMISED SENSORY QUALITY", which is the U.S. National Stage Application of International Patent Application No. PCT/FR2014/051589, filed Jun. 25, 2014, which claims the priority of French Application No. 1356113, filed Jun. 26, 2013.

The present invention relates to novel compositions of flour of microalgae of the *Chlorella* genus having an optimized sensory profile, thereby making it possible to incorporate them into food formulations without generating undesirable flavors, and also to a method for evaluating the organoleptic profile of a composition of flour of microalgae of the *Chlorella* genus.

PRESENTATION OF THE PRIOR ART

Historically requiring "only water and sunlight" to grow, algae have for a long time been considered to be a source of food.

There are several species of algae that can be used in food, most being "macroalgae" such as kelp, sea lettuce (*Ulva lactuca*) and red algae of the type *Porphyra* (cultured in Japan) or "dulse" (*Palmaria palmata*).

However, in addition to these macroalgae, there are also other algal sources represented by the "microalgae", i.e. photosynthetic or non-photosynthetic single-cell microscopic algae, of marine or non-marine origin, cultured for their applications in biofuels or food.

For example, *spirulina* (*Arthrospira platensis*) is cultured in open lagoons (under phototrophic conditions) for use as a food supplement or incorporated in small amounts into confectionery products or drinks (generally less than 0.5% weight/weight).

Other lipid-rich microalgae, including certain species of *Chlorella* type are also very popular in Asian countries as food supplements (mention is made of the omega-3-fatty-acid-producing microalgae of the *Crypthecodinium* or *Schizochytrium* genus).

The production and the use of the flour of microalgae of *Chlorella* type are, for example, described in documents WO 2010/120923 and WO 2010/045368.

The oil fraction of the microalgal flour, which may be composed essentially of monounsaturated oils, may provide nutritional and health advantages compared with the saturated, hydrogenated and polyunsaturated oils often found in conventional food products.

When it is desired to industrially produce microalgal flour powders from the biomass of said microalgae, considerable difficulties remain, not only from the technological point of view, but also from the point of view of the sensory profile of the compositions produced.

Indeed, while algal powders for example produced with algae photosynthetically cultured in exterior ponds or by photobioreactors are commercially available, they have a dark green color (associated with chlorophyll) and a strong, unpleasant taste.

Even formulated in food products or as nutritional supplements, these algal powders always give this visually unattractive green color to the food product or to the nutritional supplement and have an unpleasant fishy taste or the savor of marine algae.

Moreover, it is known that certain species of blue algae naturally produce odorous chemical molecules such as geosmin (trans-1,10-dimethyl-trans-9-decalol) or MIB (2-methylisoborneol), generating earthy or musty odors.

As for chlorellae, the descriptor commonly accepted in this field is the taste of "green tea", slightly similar to other green vegetable powders such as powdered green barley or powdered green wheat, the taste being attributed to its high chlorophyll content.

Their savor is usually masked only when they are mixed with vegetables with a strong savor or citrus fruit juices.

There is therefore still an unsatisfied need to have compositions of flour of microalgae of the *Chlorella* genus of suitable organoleptic quality and allowing the use thereof in more numerous and diversified food products.

SUMMARY OF THE INVENTION

The applicant company has found that it is possible to meet this need by providing microalgal flour compositions having an optimized sensory profile, characterized by their total content of 13 volatile organic compounds.

Thus, the present invention relates to a method for determining the organoleptic quality of a microalgal flour composition, comprising determining the total content of 13 volatile organic compounds, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

Preferably, the total content of 13 volatile organic compounds is determined by SPME/GC, preferably by SPME/GC-MS.

Thus, a low total content of 13 volatile organic compounds is associated with an optimized organoleptic quality. Conversely, a higher total content of 13 volatile organic compounds is associated with a medium, or even poor or unacceptable, organoleptic quality.

Preferably, the total content of 13 volatile organic compounds is determined by the total surface area of the chromatography peaks after SPME/GC corresponding to the 13 volatile organic compounds.

Preferably, the total content of 13 volatile organic compounds, in particular the total surface area of the chromatography peaks corresponding to the 13 volatile organic compounds, is compared to that of a reference microalgal flour composition or compositions for which the organoleptic qualities are defined, in particular as unacceptable or acceptable.

The present invention also relates to a microalgal flour composition having an optimized organoleptic quality, characterized in that its total content of 13 volatile organic compounds is low, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

Preferably, the composition is characterized in that the total surface area of the chromatography peaks after SPME/GC corresponding to the 13 volatile organic compounds is between 1% and 25% relative to that of a reference microalgal flour composition of unacceptable organoleptic quality.

The present invention also relates to a composition for tasting a microalgal flour composition, comprising:

5-10% of microalgal flour composition, preferably approximately 7%;

0.5-2% of sugar, preferably approximately 1%;

0.1-0.5% of vanilla flavoring, preferably approximately 0.25%; and the remainder being skimmed milk, preferably approximately 91.75%, the percentages being expressed by weight of the composition.

Thus, the present invention relates to a method for preparing a composition for tasting a microalgal flour composition, comprising the preparation of a tasting composition as described above, the homogenization thereof, and the heating of the composition at 60-85° C., preferably approximately 75° C., for 2-10 minutes, preferably approximately 5 minutes.

It relates to a method for testing the organoleptic qualities of a microalgal flour composition, comprising the preparation of a tasting composition as described in the present document and the evaluation of the organoleptic qualities by a panel of testers.

Finally, the present invention relates to a method for defining an analytical profile of volatile compounds making it possible to evaluate the organoleptic quality of the microalgal flour compositions, comprising:

the construction of a first matrix associating microalgal flour compositions, including two controls of acceptable and unacceptable organoleptic quality, with the evaluation of their organoleptic qualities by a sensory panel of at least 10 individuals, the construction of a second matrix associating with these same compositions their characterization by a volatile organic compound analysis profile, and the correlation of the first matrix with the second to produce a relationship model on the basis of which the compositions having an optimized organoleptic profile can thus be characterized by their analytical profile of volatile organic compounds.

Preferably, the sensory analysis descriptors comprise color, coating texture, sweetness, and the following flavors: mushroom, cereals, butter/dairy product, rancid oil and vegetable aftertaste.

Preferably, the sensory analysis is carried out using a tasting composition prepared by the method described above and explained in detail in the present document.

Preferably, the analysis of the volatile organic compounds is carried out by SPME/GC-MS.

Preferably, the volatile organic compounds belong to the families of saturated and diunsaturated aldehydes, unsaturated ketones, and carboxylic acids and derivatives thereof.

DETAILED DESCRIPTION OF THE INVENTION

For the purposes of the invention, a microalgal flour composition has an "optimized sensory profile" or an "optimized organoleptic quality" when its evaluation by a sensory panel in a food formulation (for example ice cream) concludes that there is an absence of off-notes which impair the organoleptic quality of said food formulations containing these microalgal flour compositions.

The term "organoleptic quality" is intended to mean the property of a food in terms of taste, odor, appearance, color and consistency.

These off-notes are associated with the presence of undesirable specific odorous and/or aromatic molecules which are characterized by a perception threshold corresponding to the minimum value of the sensory stimulus required to arouse a sensation.

The "optimized sensory profile" or "optimized organoleptic quality" is then reflected by a sensory panel by obtaining the best scores on a scale of evaluation of the 4 sensory criteria (appearance, texture, savors and flavors).

The term "total content" is intended to mean the sum of the contents of each of the volatile organic compounds of the list.

The term "approximately" is intended to mean the value plus or minus 10% thereof, preferably plus or minus 5% thereof. For example, "approximately 100" means between 90 and 110, preferably between 95 and 105.

The applicant company has discovered that the sensory profile of a microalgal flour composition can also be defined by the nature and the threshold of detection of odorous specific molecules, in particular of specific volatile organic compounds. Indeed, it has identified a set of 13 volatile organic compounds, the overall content of which in a microalgal flour composition makes it possible to determine the organoleptic quality thereof. These 13 volatile organic compounds are the following: heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

Thus, the present invention relates to a method for determining the organoleptic quality of a microalgal flour composition, comprising determining the total content of 13 volatile organic compounds, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

The method does not exclude the determination of the content of other volatile organic compounds. However, the 13 volatile organic compounds are sufficient to determine the organoleptic quality of a microalgal flour composition.

Preferably, these volatile organic compounds are sampled by solid phase microextraction (SPME) and analyzed by gas chromatography GC, in particular by GC-MS (gas chromatography-mass spectrometry).

The volatile fraction is extracted from the sample of the microalgal flour composition by heating said composition for a sufficient period of time in the presence of an SPME fiber. The fiber may, for example, be chosen, non-exhaustively, from the group consisting of carboxen and polydimethylsiloxane (CAR/PDMS), divinylbenzene, carboxen and polydimethylsiloxane (DVB/CAR/PDMS), an alloy of metal and of polydimethylsiloxane (PDMS), a Carbopack-Z® fiber (graphitized carbon black), polyacrylate, Carbowax® polyethylene glycol (PEG), and PDMS/DVB. Preferably, a DVB/CAR/PDMS fiber is used.

For example, the extraction can be carried out at a temperature between 40 and 70° C., preferably between 50 and 65° C., in particular approximately 60° C. for at least 10 minutes, preferably at least 15 minutes and for example between 15 minutes and 1 hour.

Preferably, this extraction step is carried out in a sealed container. A sufficient amount of sample must be used, for example at least 1 g, in particular between 1 and 10 g and in particular approximately 3 g. The SPME technique is well known to those skilled in the art and is part of the general knowledge thereof.

The volatile organic compounds are then desorbed at a temperature compatible with the type of SPME fiber used, for example between 250 and 270° C. for the fiber used in our tests, more specifically at 250° C., and injected into the analysis system.

Preferably, the analysis is carried out by gas chromatography GC, in particular by GC-MS.

Several GC/MS devices are commercially available, for example the GC/Mass Clarus spectrometer (PerkinElmer, USA), the Hewlett Packard 6890 gas chromatograph (Hewlett Packard, USA) and the Aglient 6890N gas chromatograph coupled to the Aglient 5973 selective mass detector. The ionization methods which can be used in GC/MS are for example mass spectrometry with electron impact ionization (EI), chemical impact ionization (CI), electrospray ionization, matrix-assisted laser desorption/ionization (MALDI), luminescent discharge, field desorption (FD), etc.

The columns used for the GC are preferably a Cp-Wax 52CB 60 m*0.32 mm column; df 0.25 µm or equivalent which we retained; another column tested was one of ZB-1 ms 30 m*0.25 mm type; df 1 µm.

Thus, the height or the surface area of the chromatography peak corresponding to the volatile organic compound correlates with the amount of said compound. The term "surface area of the peak" is intended to mean the surface area of a specific ion under the curve in the SPME-GC/MS chromatogram.

Preferably, the content of one of the 13 volatile organic compounds is determined by the surface area of the peak of the specific ion of the SPME-GC/MS chromatogram corresponding to this volatile organic compound.

In addition, the total content of 13 volatile organic compounds is preferably determined by the total surface area of the chromatography peaks after SPME/GC corresponding to the 13 volatile organic compounds.

The content of volatile organic compounds is determined, in particular in comparison with that of a reference product. Preferably, the total content of volatile organic compounds of the list of the 13 defined in the present invention is considered.

Thus, a low total content of 13 volatile organic compounds is associated with an optimized organoleptic quality. Conversely, a higher total content of 13 volatile organic compounds is associated with a medium, or even poor or unacceptable, organoleptic quality.

In a first embodiment, the reference product is a product in which the amount of a volatile organic compound is known.

Ideally, the reference product could comprise the 13 volatile organic compounds of the list in predefined amounts. Such a reference product makes it possible to exactly determine the amount of the volatile organic compounds.

In a second embodiment, the reference product is a microalgal flour composition, the organoleptic profile of which is defined. The organoleptic profile is preferably determined by the method described in detail later in the present document or in the experimental section. Thus, this reference product makes it possible to determine relative amounts of volatile organic compounds.

In this embodiment, when the reference microalgal flour composition has an organoleptic profile which is acceptable or only just acceptable, the content of volatile organic compounds, preferably the total content of said 13 volatile organic compounds, is compared to that determined for the reference product. If it is greater than or equal to that of the reference product, then the composition tested is considered to have an insufficient or unacceptable organoleptic quality. If it is less, then the composition tested is considered to have an acceptable or optimized organoleptic quality.

In this embodiment, when the reference microalgal flour composition has an organoleptic profile which is unacceptable, or even very unacceptable, the content of volatile organic compounds, preferably the total content of said 13 volatile organic compounds, is compared to that determined for the reference product. If it is greater than or equal to that of the reference product, then the composition tested is considered to have an insufficient or unacceptable organoleptic quality. If it is less, then the composition tested is considered to have an acceptable or optimized organoleptic quality. In particular, it has been defined in the examples, using a reference microalgal flour composition having a very unacceptable organoleptic profile, that the composition tested has an optimized organoleptic profile when the total content of said 13 volatile organic compounds is between 1% and 25% relative to that of this reference composition (which is considered to be 100%). For example, the total content of a composition with an acceptable organoleptic quality is at least two times less than that of a composition with an unacceptable organoleptic quality, for example at least 2, 3 or 4 times less, and in a most demanding embodiment, at least 10 times less.

In one preferred embodiment, the content of said 13 volatile organic compounds, in particular their total content, is considered in the method, this being after SPME/GC-EI/MS.

The invention thus makes it possible to classify the microalgal flour compositions according to their organoleptic quality, and to qualify the food formulations containing them, by quantifying said particular volatile organic compounds.

The present invention also relates to a microalgal flour composition having an optimized organoleptic quality, characterized in that its total content of 13 volatile organic compounds is low, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

Indeed, it has been determined by the applicant company's studies that, the lower the total content of 13 volatile organic compounds, the better the organoleptic quality of the microalgal flour composition. Conversely, the higher the total content of 13 volatile organic compounds, the poorer the organoleptic quality of the microalgal flour composition.

The content of volatile organic compounds is determined as detailed above in the method for evaluating the organoleptic quality of a microalgal flour composition. This content is evaluated relative to that of a reference product as defined above.

For example, the total content of said volatile organic compounds is low in comparison with a microalgal flour composition having an unacceptable, or even very unacceptable, organoleptic quality. For example, the total content of a composition with an acceptable organoleptic quality is at least two times less than that of a composition with an unacceptable organoleptic quality, for example at least 2, 3 or 4 times less, and in a most demanding embodiment, at least 10 times less. Preferably, the composition is characterized in that the total surface area of the chromatography peaks after SPME/GC corresponding to the 13 volatile organic compounds is between 1% and 25% relative to that of a reference microalgal flour composition of unacceptable organoleptic quality.

The term "microalgal flour composition" is intended to mean a composition comprising at least 50%, 60%, 70%, 80% or 90% by dry weight of microalgal biomass. However, other ingredients can optionally be included in this composition.

For the purposes of the present invention, the term "microalgal flour" should be understood in its broadest interpretation and as denoting, for example, a composition comprising a plurality of particles of microalgal biomass. The microalgal biomass is derived from microalgal cells, which may be whole or broken, or a mixture of whole and broken cells.

A certain number of prior art documents, such as international patent application WO 2010/120923, describe methods for the production and use in food of *Chlorella* microalgal biomass.

The microalgae of which it is a question in the present invention are therefore microalgae of the *Chlorella* genus, more particularly *Chlorella protothecoides*, even more particularly *Chlorella* deprived of chlorophyll pigments, by any method known per se to those skilled in the art (either because the culture is carried out in the dark, or because the strain has been mutated so as to no longer produce these pigments). In particular, the microalgae can be chosen, non-exhaustively, from *Chlorella protothecoides*, *Chlorella kessleri*, *Chlorella minutissima*, *Chlorella* sp., *Chlorella sorokiniama*, *Chlorella luteoviridis*, *Chlorella vulgaris*, *Chlorella reisiglii*, *Chlorella ellipsoidea*, *Chlorella saccarophila*, *Parachlorella kessleri*, *Parachlorella beijerinkii*, *Prototheca stagnora* and *Prototheca moriformis*. Thus, in one quite particular embodiment, the microalgal flour composition is a *Chlorella* flour composition, and in particular a *Chlorella protothecoides* flour composition.

The fermentative process described in this patent application WO 2010/120923 thus allows the production of a certain number of microalgal flour compositions of variable sensory quality. The method as described in the present document therefore makes it possible to select the microalgal flour compositions which have an acceptable organoleptic profile, in particular for food applications, without having to organize organoleptic evaluations by a panel of individuals in order to do so.

The present invention also relates to a composition for tasting microalgal flour compositions. Indeed, the applicant company has defined a very simple tasting matrix. Nevertheless, it makes it possible to carry out an organoleptic evaluation similar to that obtained with much more complex and very different recipes, such as an ice cream or a brioche. The evaluation with this tasting matrix is much more precise or accurate than that carried out with a simple aqueous solution, which has proved to be incapable of predicting the organoleptic qualities of microalgal flour compositions in an ice cream, for example.

Consequently, the present invention relates to a composition for tasting microalgal flour compositions, comprising:
  5-10% of microalgal flour composition, preferably approximately 7%;
  0.5-2% of sugar, preferably approximately 1%;
  0.1-0.5% of vanilla flavoring, preferably approximately 0.25%; and
  the remainder being skimmed milk, preferably approximately 91.75%,
  the percentages being expressed by weight of the composition.

Moreover, the present invention relates to a method for preparing the composition for tasting a microalgal flour composition, comprising the preparation of a tasting composition as described above, the homogenization thereof, and the heating of the composition at 60-85° C., preferably approximately 75° C., for 2-10 minutes, preferably approximately 5 minutes.

It also relates to a method for testing the organoleptic qualities of a microalgal flour composition, comprising the preparation of a tasting composition as described above and the evaluation of the organoleptic qualities by a panel of testers. This evaluation can in particular be carried out by the methods detailed below.

The applicant company also provides a method for defining an analytical profile of volatile compounds making it possible to evaluate the organoleptic quality of the microalgal flour compositions, comprising:
  the construction of a first matrix associating microalgal flour compositions, including preferably two controls of acceptable and unacceptable organoleptic quality, with the evaluation of their organoleptic qualities by a sensory panel of at least 10 individuals,
  the construction of a second matrix associating with these same compositions their characterization by a volatile organic compound analysis profile, and
  the correlation of the first matrix with the second to produce a relationship model on the basis of which the compositions having an optimized organoleptic profile can thus be characterized by their analytical profile of volatile organic compounds.

A sensory panel is formed in order to evaluate the sensory properties of various batches of microalgal flour compositions, in particular *Chlorella protothecoides* biomass flour compositions.

A set of individuals, at least 10, 20 or 30, in particular approximately 15, is brought together to evaluate descriptors of several microalgal flour compositions, preferably in comparison with a sample of reference microalgal flour identified as complying, i.e. of acceptable organoleptic quality (reference batch No. 1) and another sample of very unacceptable organoleptic quality (reference batch No. 2).

Preferably, the microalgal flour compositions are tested in the form of a tasting composition according to the present document. Alternatively, the compositions can be tested in any other form desired by those skilled in the art, for example in the form of an ice cream or of a breadmaking product such as a brioche.

Preferably, the reference products as presented in the following table are associated with each descriptor:

|  | Descriptors | Reference |
| --- | --- | --- |
| Appearance | Color (from light to dark) |  |
| Texture | Coating | Whole milk + 5% cream |
| Savors | Sweet | 1% sucrose |
| Flavors | Mushroom | 100 g of mushrooms in 100 ml of cold water/X 4 dilution |
|  | Cereals | 10% Ebly Solution |
|  | Butter/dairy product |  |
|  | Rancid oil | 1.5% Oxidized oil |
|  | Vegetable aftertaste | Very unacceptable microalgal flour composition |

Of course, those skilled in the art can define other reference products if they so desire.

At each tasting session, several products, for example 4 to 5, are evaluated with regard to each descriptor in comparison with a reference sample or batch, preferably of reference considered to be of acceptable organoleptic quality.

All the products are evaluated one after the other, on scales ranging, for example, from 1 to 9 in the following way:

Value of 1: the descriptor evaluated is not present in the product;

Value of 5: the descriptor evaluated is present in the product in exactly the same way as on the reference product of acceptable organoleptic quality;

Value of 9: the descriptor evaluated is very present in the product.

The reference batch of acceptable organoleptic quality is a microalgal flour composition that complies in the sense that it has the sensory profile "satisfying" all these descriptors. The reference batch of very unacceptable organoleptic quality is a batch which does not satisfy the descriptors relating to the aromatic notes, i.e. to the savor and flavor descriptors, since it has a considerable vegetable aftertaste.

It is important to note that the reference batch of acceptable organoleptic quality is not necessarily the microalgal flour composition having the optimal sensory profile: it is preferably a microalgal flour composition perceived by the sensory panel as "satisfactory", in particular having a grade of 5 on all the descriptors tested.

In this embodiment, the other microalgal flour compositions, the compositions tested, are classified by the sensory panel on either side of this reference batch of acceptable organoleptic quality.

Generally, the other compositions tested are classified by the sensory panel relative to the reference batch(es) of acceptable or unacceptable, preferably acceptable, organoleptic quality.

Thus, the first step results in the classification of the various microalgal flour compositions tested according to their organoleptic quality.

In particular, analyses of variance (ANOVAs) are carried out in order to evaluate the discriminating capacity of the descriptors (descriptors of which the p-value associated with the Fisher test—type-3 ANOVA—is less than 0.20 for the Composition effect in the model descriptor~Composition+judge). The Composition effect is interpreted as the discriminating capacity of the descriptors: if there is no effect (Critical Probability>0.20), the compositions were not discriminated according to this criterion. The smaller this critical probability, the more discriminating the descriptor. A principal component analysis (PCA) is then carried out in order to obtain sensory mapping of the compositions, and a simultaneous representation of all the compositions regarding all the descriptors.

This classification therefore then serves as a basis for studying the analytical profile of the volatile organic compounds and selecting molecules responsible for the poor organoleptic quality of the microalgal flour compositions.

Thus, the profile of the volatile organic compounds of the microalgal flour compositions is determined. It is determined by any method known to those skilled in the art, and preferably by SPME/GC-MS, as detailed above.

In one very specific example, for the SPME/GC-MS analysis of the various batches of microalgal flour compositions, the process is carried out as follows.

A test specimen of 3 g of sample is introduced into a sealed SPME flask (20 ml) and incubated at 60° C. for 15 min and then extracted at 60° C. for 45 min with a DVB/CAR/PDMS (abbreviation for divinylbenzene/carboxen/polydimethylsiloxane, df 50/30 μm) SPME fiber.

The volatile organic compounds extracted are desorbed at 250° C. in the injector of the TSQ GC-MS system from Thermo Scientific, injected in "splitless" mode and then separated on a CPwax52 (60 m×0.25 mm, 0.25 μm) column with helium gas at 1.5 ml/min. The temperature program is: 50° C. isotherm for 3 min, then programming at 5° C./minute up to 230° C., then isotherm for 20 min. The detection is carried out by electron impact (EI) mass spectrometry and the compounds are identified by comparison with the EI spectra of the NIST library.

The analysis of the volatile compounds gives very complex GC-MS chromatograms, with a very large number of peaks. By means of analyses of variance and linear regressions, the volatile organic compounds which correlate best with the results obtained for the sensory matrix and with the off-notes are selected. Preferably, the volatile organic compounds belong to 4 families of compounds: aldehydes (saturated and unsaturated), unsaturated ketones, carboxylic acids and carboxylic acid derivatives.

Thus, an optimized organoleptic profile is associated and characterized by an analytical profile of volatile organic compounds.

In one preferred embodiment, the various organic compounds selected will be considered in terms of their total content, in comparison with reference compositions, in particular as defined above. In particular, the total surface area of the chromatography peaks corresponding to the volatile organic compounds selected will be considered and compared.

The invention will be understood more clearly from the examples which follow, which are intended to be illustrative and nonlimiting.

EXAMPLES

Example 1. Definition of the Sensory Test

Sensory Test Conventionally Carried Out

The perception of a microalgal flour composition is generally determined by solubilization in water, the neutral medium par excellence.

A sensory panel was therefore formed to evaluate the sensory properties of various batches of microalgal flour, prepared according to the teaching of patent application WO 2010/12093.

Eight batches of microalgal flour were tested: batch 21, batch 23, batch 24, batch 31, batch 53, batch 61, batch 111 and batch 131, in comparison with a reference sample identified as complying or acceptable (reference batch No. 1) and another, very unacceptable, batch (reference batch No. 2).

A set of 14 individuals were brought together to produce descriptors with respect to a microalgal flour composition considered to be complying (reference batch 1), said composition being placed in aqueous solution at 10% at ambient temperature (until homogenization).

The list of descriptors retained is the following:

Appearance: Color

Texture: Coating

Savors: Sweet, Bitter

Flavors: mushroom, cereal, butter/dairy products, rancid oil

Table 1 below presents the reference products associated by the panel with each descriptor:

TABLE 1

|  | Descriptors | Reference |
|---|---|---|
| Appearance | Color (from light to dark) | |
| Texture | Coating | Whole milk + 5% cream |
| Savors | Sweet | 1% sucrose |
|  | Bitterness | Quinine 0.0075 g/l |
| Flavors | Mushroom | 100 g of mushrooms in 100 ml of cold water/X 4 dilution |
|  | Cereals | 10% EBLY wheat solution |
|  | Butter/dairy product | |
|  | Rancid oil | 1.5% Oxidized oil |

At each tasting session, 4 to 5 compositions are evaluated with regard to each descriptor in comparison to a composition identified as being acceptable (reference batch 1).

All the compositions are evaluated one after the other, on scales ranging from 1 to 9.

1: the descriptor evaluated is not present in the product
5: the descriptor evaluated is present in the product in exactly the same way as on the reference product 1
9: the descriptor evaluated is very present in the product.

For example, the "sweet" descriptor is evaluated as follows:

|  |  |  |  | Reference |  |  |  |  |
|---|---|---|---|---|---|---|---|---|
| 1 | 2 | 3 | 4 | 5 | 6 | 7 | 8 | 9 |

Table 2 below presents the results of the sensory analyses performed by the Panel on 6 different batches of microalgal flour compositions of variable organoleptic quality:

TABLE 2

|  | Sensory test in solution |
|---|---|
| Reference batch 1 | Acceptable |
| Batch 24 | Acceptable |
| Batch 53 | Acceptable |
| Batch 61 | Unacceptable |
| Batch 111 | Acceptable |
| Batch 131 | Acceptable |

It appears that 5 of the 6 batches tested have an organoleptic quality similar to the control, which would appear to indicate that the method for producing them is sufficiently managed to result in the obtaining of compositions of "acceptable" organoleptic quality.

Tests in ice cream applications were then carried out in order to verify the relevance of the classification of the microalgal flour compositions according to the preceding test.

The ice cream formulation is the following:

| INGREDIENTS | Amount (%) |
|---|---|
| Skimmed milk | 64.42 |
| Sucrose | 13.5 |
| Crème fraîche (36% fat) | 10.5 |
| Algal composition batches | 4 |
| Powdered skimmed milk | 3.5 |
| ROCLYS ® 4080 sold by ROQUETTE FRERES | 3 |
| Stabilizer (CREMODAN ® SE30) | 0.55 |
| Vanilla flavoring IFF 10836706 | 0.5 |
| Salt | 0.03 |
| Total (%) | 100 |

A triangular test (as described in standard NF V09-013 from July 1983) is undertaken by forming a sensory panel consisting of 21 individuals who are asked to give their opinion on the organoleptic quality of two batches of ice cream produced from:
reference batch 1 and
a batch chosen from the range of which the assessment in the preceding sensory test (solubilization in water) was judged to be acceptable: in this case batch 24.

One of the 2 ice creams is presented in duplicate to the panelists.

They are then asked whether they notice a difference between these three ice creams.

As it happens, 14 individuals out of 21 succeeded in noticing a difference; the panel therefore noticed, against all expectations, in the context of the ice cream, an organoleptic difference between the reference batch and the tested batch nevertheless judged to be acceptable in the sensory test on the powder solubilized in water.

The difference is significant between the two compositions (binomial distribution B (21, ⅓), with a significance threshold of 0.05). Moreover, 7 individuals also noticed a strong aftertaste to describe this production batch.

Tests were then undertaken on a certain number of product batches.

Table 3 below summarizes the results obtained.

TABLE 3

|  | Sensory test in solution | In ice cream application |
|---|---|---|
| Reference batch 1 | acceptable | acceptable |
| Batch 24 | acceptable | unacceptable |
| Batch 53 | acceptable | unacceptable |
| Batch 61 | unacceptable | unacceptable |
| Batch 111 | acceptable | acceptable |
| Batch 131 | acceptable | acceptable |

It is deduced therefrom that the conventional test for measuring the organoleptic quality of a microalgal flour composition in water is not suitable for predicting the organoleptic quality of the corresponding ice creams.

Similar results were obtained in the case of brioches prepared from these same microalgal flour compositions.

Test Developed by the Applicant Company for Evaluating Various Microalgal Flour Compositions According to the Invention Given the aforementioned, the applicant company chose to develop its own test by replacing the complex tasting matrix used for the ice cream formulation with a mixture that is simpler to prepare than the ice cream but more discriminating than the solution at 10% in water.

The recipe formulated is the following:
7% of microalgal flour composition
1% granulated sugar
0.25% household vanilla flavoring
91.75% skimmed milk.

The mixture is homogenized with an immersion mixer until a homogeneous mixture is obtained (approximately 20 seconds) and is then heated at 75° C. for 5 minutes in a water bath.

The bitter descriptor was removed since it was no longer coherent in this new matrix and a new descriptor was added:

| Descriptors | | Reference |
|---|---|---|
| Flavors | Vegetable aftertaste | Microalgal flour composition identified as very unacceptable (reference batch 2) |

The evaluation method remains the same (use of scales, reference at 5).

Data Processing Software

The analyses were carried out using the R software (freely sold):

R version 2.14.1 (2011 Dec. 22)

Copyright (C) 2011 The R Foundation for Statistical Computing

ISBN 3-900051-07-0

Platform: i386-pc-mingw32/i386 (32-bit)

The software is a working environment which requires the loading of modules containing the calculation functions.

The modules used in this study are the following:

For the PCA: Package FactoMineR version 1.19

For the ANOVA: Package car version 2.0-12

For the Linear Regression: Package stats version 2.14.1

Data Processing:

Analyses of variance (ANOVAs) are carried out in order to evaluate the discriminating capacity of the descriptors (descriptors of which the p-value associated with the Fisher test—type-1 ANOVA—is less than 0.20 for the Composition effect in the model descriptor~composition+judge).

The "composition" effect is interpreted as the discriminating capacity of the descriptors: if there is no effect (Critical Probability>0.20), the compositions were not discriminated according to this criterion. The smaller this critical probability, the more discriminating the descriptors.

A principal component analysis (PCA) is then carried out in order to obtain sensory mapping of the compositions, and also a simultaneous representation of all the compositions regarding all the descriptor.

Various batches (batch 21, batch 23, batch 24, batch 31, batch 53, batch 61, batch 111 and batch 131) were analyzed according to the method described above.

Two examples regarding the descriptors "butter/dairy products" and "vegetable aftertaste" are presented here.

| "Vegetable aftertaste" Analysis of variance table | | | | | |
|---|---|---|---|---|---|
| | Df | Sum Sq | Mean Sq | F value | Pr(>F) |
| Composition | 9 | 109.693 | 12.1881 | 18.2423 | <2e-16 |
| Judge | 13 | 18.732 | 1.4409 | 2.1566 | 0.01298 |
| Residues | 185 | 123.603 | 0.6681 | — | |

| "Butter/dairy products" Analysis of variance table | | | | | |
|---|---|---|---|---|---|
| | Df | Sum Sq | Mean Sq | F value | Pr(>F) |
| Composition | 9 | 8.292 | 0.92131 | 1.4530 | 0.1699 |
| Judge | 13 | 8.235 | 0.63347 | 0.9991 | 0.4547 |
| Residues | 160 | 101.451 | 0.63407 | — | |

It appears that the critical probabilities associated with the composition effect for the 2 descriptors studied are less than 0.2: the 2 descriptors are therefore discriminating. The critical probability is smaller with regard to the "vegetable aftertaste" descriptor than with regard to the "butter/dairy products" descriptor, thereby signifying that a greater difference is observed between the compositions with regard to the first criterion than with regard to the second.

Below is a table summing up the critical probabilities obtained for the composition and judge effects for all the descriptors.

| | Composition | judge |
|---|---|---|
| Color | 1.62E−31 | 1.16E−05 |
| vegetable aftertaste | 1.60E−21 | 1.30E−02 |
| Rancid oil taste | 4.00E−06 | 9.00E−04 |
| Coating | 1.48E−05 | 1.63E−02 |
| Cereals | 4.05E−04 | 1.94E−07 |
| Mushrooms | 1.37E−03 | 5.66E−05 |
| Sweet | 3.23E−03 | 4.02E−04 |
| Dairy products | 1.70E−01 | 4.55E−01 |

All the descriptors are discriminating; they are all kept for establishing the PCA.

Figure 1:
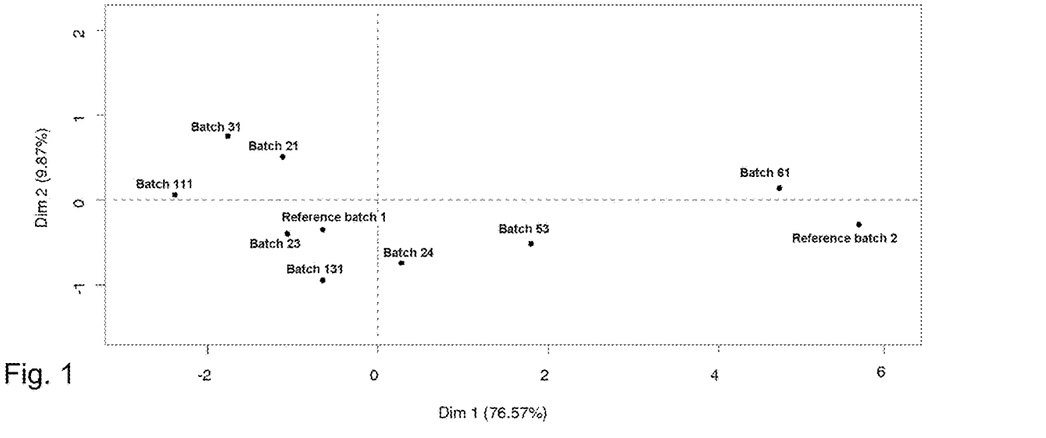
FIG. 1: Graphic representation of the various batches (cloud of points) of the PCA
Figure 2:
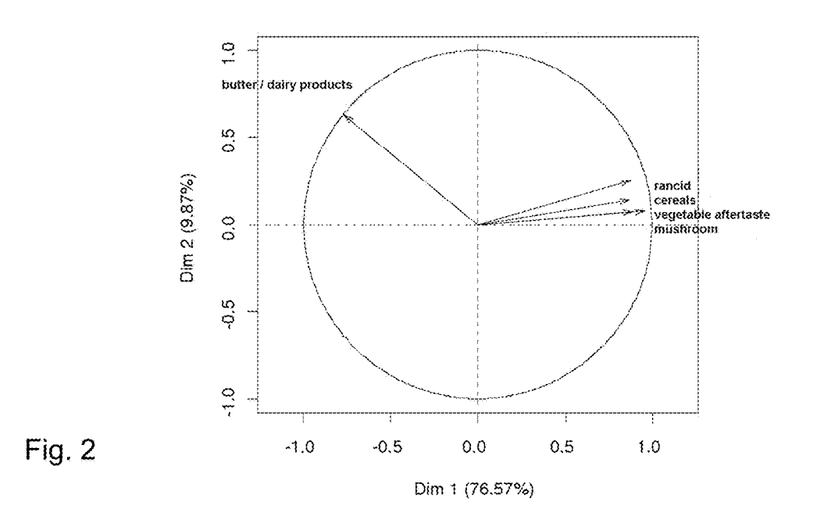
FIG. 2: Circle of correlation of the PCA representing the aromatic profiles of the various batches

Since the aromatic is an essential criterion of the compositions, the PCA was carried out regarding the descriptors relating to the flavors only (mushroom, cereals, vegetable aftertaste, dairy product, rancid). The graphic representation of this PCA is provided in FIGS. 1 and 2.

Since the first axis of the PCA summarizes more than 75% of the information (FIG. 1), it is the coordinates of the products on this axis which we use as "variable/classification". This classification therefore clearly gives an account of the sensory distances between the products.

This method makes it possible to establish a classification of the organoleptic quality of various microalgal flour compositions, which can be represented as follows: Batch 111>batch 31>batch 21>batch 23>reference batch 1>batch 131>batch 24>batch 53>batch 61>reference batch 2.

There is a clear separation between, on the one hand, batches 111, 31, 21, 23 and 131 and, on the other hand, batches 24, 53 and 61.

From an overall point of view, the panel judged batches 111, 31, 21, 23 and 131 to be acceptable and batches 24, 53 and 61 to be unacceptable.

This organoleptic classification having now been established, it is possible, efficiently according to the invention, to analyze the SPME/GC-MS profile of these samples in order to identify the reference molecular targets that will make it possible to define the quality of the compositions produced.

Example 2. Identification of the Volatile Organic Compounds (VOCs), by SPME/GC-MS, Associated with Unacceptable Off-Notes Organoleptic Classifications In order to carry out the SPME/GC-MS analysis of the various batches of microalgal flour compositions, the process is carried out as follows.

A test specimen of 3 g of sample is introduced into a sealed SPME flask (20 ml) and incubated at 60° C. for 15 min and then extracted at 60° C. for 45 min with a DVB/CAR/PDMS (abbreviation for divinylbenzene/carboxen/polydimethylsiloxane, df 50/30 µm) SPME fiber.

The volatile organic compounds extracted are desorbed in the injector of the TSQ GC-MS system from Thermo Scientific, and then separated on a CPwax52 (60 m×0.25 mm, 0.25 µm) column with helium gas at 1.5 ml/min.

The temperature program is: 50° C. isotherm for 3 min, then programming at 5° C./minute up to 230° C., then isotherm for 20 min.

The detection is carried out by electron impact (EI) mass spectrometry and the compounds are identified by comparison with the EI spectra of the NIST library.

The analysis of the volatile compounds by SPME/GC-MS gives complex chromatograms, with a very large number of molecules.

Figure 3:
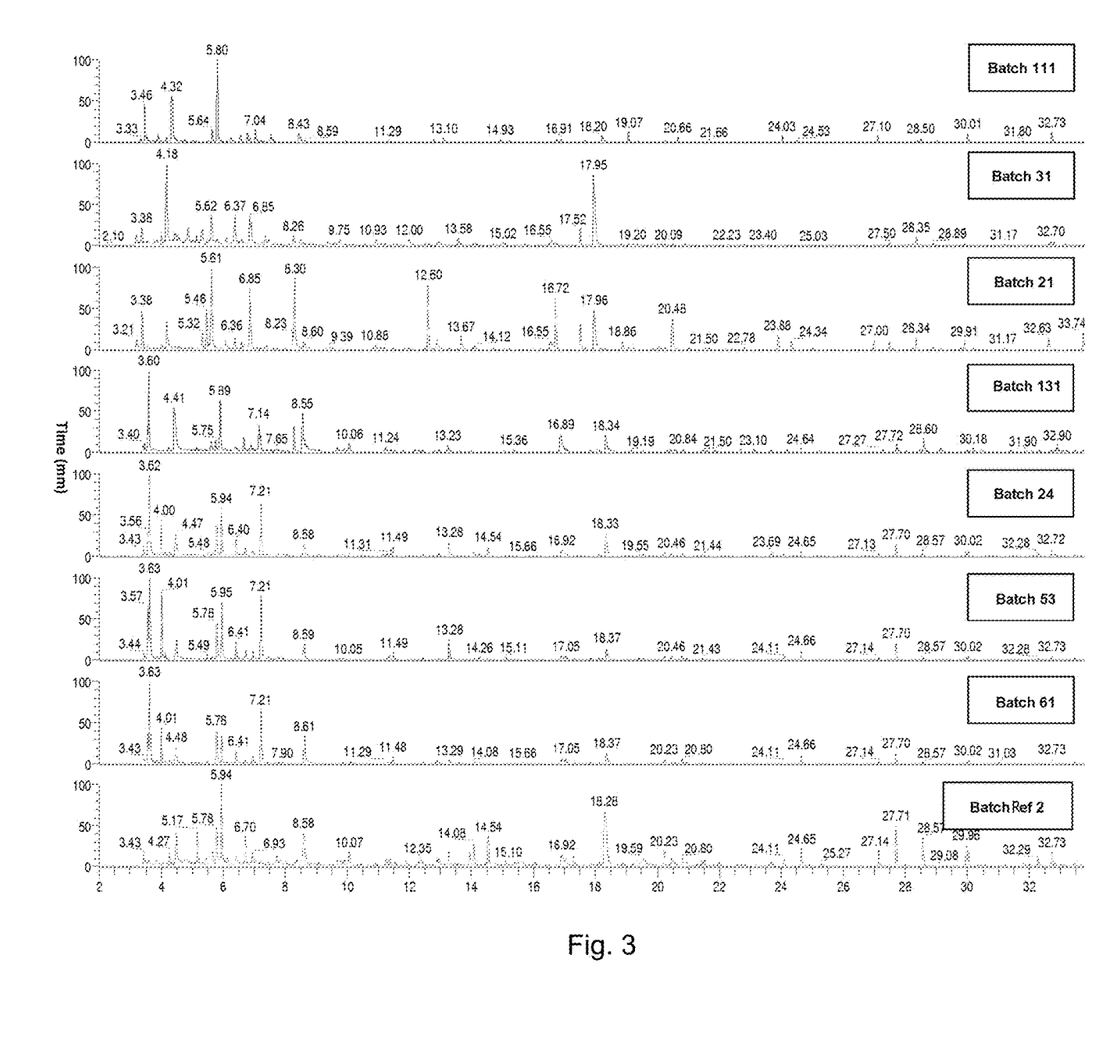
FIG. 3: Chromatographic profiles representing the relative absorbances as a function of time for the various batches tested. The arrow represents the sensory classification from good (at the top) to bad (at the bottom).

A first approach consists in comparing the chromatographic profiles (FIG. 3) and determining whether these relatively "crude" results enable a link to be made with the sensory classification as presented in example 1.

Visually, the chromatographic profiles of the volatile compounds of the various samples do not simply reflect the sensory classification.

On the other hand, integration of the surface areas of the chromatographic peaks between 3.2 and 33.5 min makes it possible to achieve this.

However, the error in the SPME/GC-MS analysis is considerable (standard deviation of approximately 30%); it is therefore not easy to differentiate the samples classified as "good" from the samples classified as "poor".

1st Approach

Since not all the volatile compounds reflect the sensory classification finely enough, it is decided firstly to identify and select two volatile molecules present in the headspace of the samples which may be responsible for the sensory descriptors: nonanal and 2,4-decadienal which are lipid degradation compounds well known for their sensory impact.

It is possible to introduce a notion of "flavor value" (FV) by taking into account the known olfactory threshold of these compounds, according to the following formula:

$FVx$=Concentration of the compound $x$/olfactory threshold of the compound $x$ with 0.07 ppb for the olfactory threshold in water of trans-2-trans-4-decadienal, and 1 ppb for nonanal.

The total FV then corresponds to the sum of the individual FVs of the compounds x taken into account.

Figure 4:
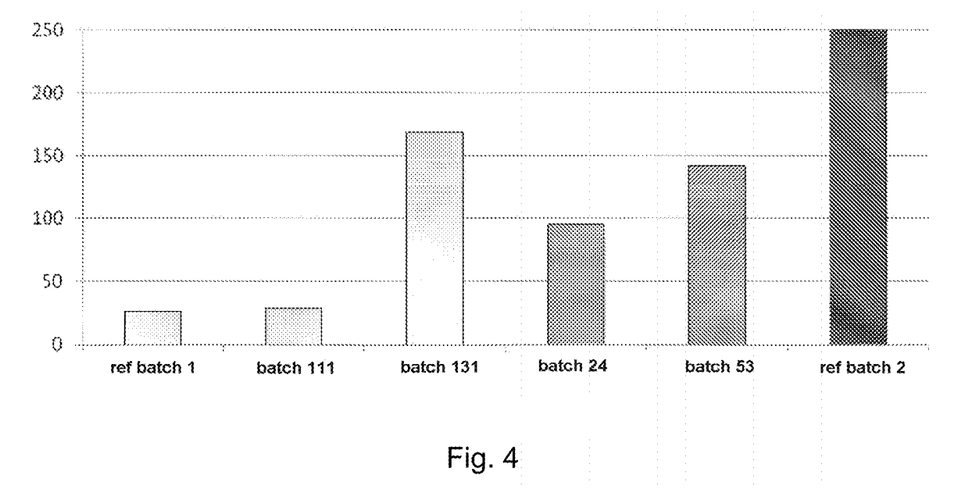
FIG. 4: Flavor values of the batches tested, considering nonanal and t,t-2,4-decadienal.

On first analysis, this model appears to be coherent with the sensory evaluation of the various samples, but unfortunately not all (FIG. 4).

Consequently, it is not possible to correlate the sensory profile measured for each batch in comparison with the flavor value of the two arbitrarily chosen compounds.

2nd Approach

A second approach consists in adding to the list of volatile organic compounds of the above model by listing the volatile compounds identified on the SPME/GC-MS chromatogram which appear to accompany the unacceptable off-notes organoleptic classifications, in total 35: pentanal, diacetyl, hexanal, 3-penten-2-one, heptanal, 2-pentylfuran, acetone, acetol, 2-heptenal, 3-octen-2-one, nonanal, acetic acid, 2-ethyl-1-hexanol, 2,4-heptadienal, 3,5-octadien-2-one, benzaldehyde, 2-nonenal, butanoic acid, isovaleric acid, 2,4-nonadienal, 5,6-dihydro-2H-pyran-2-one, pentanoic acid, 2,4-decadienal, hexanoic acid, geranyl acetone, benzyl alcohol, phenylethyl alcohol, 2-ethylhexanoic acid, heptanoic acid, myristate-1, octanoic acid, triacetin, nonanoic acid, laurate-1, and myristate-2.

On the other hand, for the following models, the olfactory thresholds in water of certain molecules not known to those skilled in the art were defined by the applicant company.

In order to select the representative volatile organic compounds, a series of analyses of variance are carried out so as to keep only the volatile organic compounds which actually differ from one composition to the other given the variability of the SPME-GC/MS measurement.

The model is the following: Volatile organic compound—Composition; only the compounds for which the critical probability associated with the Fisher test is less than 0.05 are retained.

Two examples of ANOVA on the compounds acetic acid and 2-ethyl-1-hexanol are presented here.

| Anova table (Type-III Test) Acetic acid | | | | |
|---|---|---|---|---|
| | Sum Sq | Df | F value | Pr(>F) |
| (Ordinate at the origin) | 5.3107e+18 | 1 | 56.504 | 0.0842 . |
| Composition | 2.7508e+18 | 9 | 3.252 | 0.4073 |
| Residues | 9.3988e+16 | 1 | | |

Significance codes: 0 '*' 0.001 '' 0.01 '*' 0.05 '.' 0.1 ' ' 1

| Anova table (Type-III Test) 2-ethyl-1-hexanol | | | | |
|---|---|---|---|---|
| | Sum Sq | Df | F value | Pr(>F) |
| (Ordinate at the origin) | 2.8608e+16 | 1 | 2990.30 | 0.01164 * |
| Composition | 2.0894e+16 | 9 | 242.67 | 0.04978 * |
| Residues | 9.5669e+12 | 1 | | |

Significance codes: 0 '*' 0.001 '' 0.01 '*' 0.05 '.' 0.1 ' ' 1

It appears on the first volatile organic compound (acetic acid) that the composition effect is not significant (critical probability=0.40), which signifies that there is no significant difference between the products given the variability of the measurement.

On the $2^{nd}$ compound (2-ethyl-1-hexanol), the composition effect is clearly significant (critical probability<0.05).

The 2-ethyl-1-hexanol, but not the acetic acid, will therefore be kept for the study.

After this first selection of volatile compounds, linear regression models are established: this involves explaining the "sensory classification" variable by each compound one by one.

As many models as there are compounds are therefore constructed. The model is the following: Classification~Compound.

In order to select the final list of compounds identified as responsible for the unacceptable off-notes organoleptic classifications observed, only the compounds for which the critical probability associated with Student's test is less than 0.05 (test for nullity of the linear regression coefficient) will be kept.

The $R^2$ associated with the model is an indicator for quantifying the percentage of variability explained by the compound. It may not be very high, but significant; for this reason, it is chosen to select the compounds according to the critical probability (so as not to neglect a compound which has little but significant influence on the sensory classification).

Coefficients:

|  | Estimated | Std Error | t value | Pr(>|t|) |
|---|---|---|---|---|
| (Ordinate at the origin) | 5.689e−01 | 1.112e+00 | 0.512 | 0.621 |
| 2-ethyl-1-hexanol | −2.295e−09 | 1.710e−08 | −0.134 | 0.896 |

Residual standard error: 2.473 on 9 degrees of freedom
Multiple $R^2$: 0.001998 adjusted $R^2$: −0.1089
Statistic F: 0.01801 on 1 and 9 degrees of freedom, p value: 0.8962

In this example on 2-ethyl-1-hexanol, the critical probability is greater than 0.05 and there is therefore no linear link between the compound and the sensory classification established.

Coefficients:

|  | Estimated | Std. Error | T value | Pr(>|t|) |
|---|---|---|---|---|
| (Ordinate at the origin) | −8.642e−01 | 2.729e−01 | −3.167 | 0.0114 * |
| 3-octen-2-one | 5.336e−08 | 5.812e−09 | 9.181 | 7.25e−06 *** |

Significance codes: 0 '*' 0.001 '' 0.01 '*' 0.05 '.' 0.1 ' ' 1
Residual standard error: 0.7688 on 9 degrees of freedom
Multiple $R^2$: 0.9035, adjusted $R^2$: 0.8928
Statistic F: 84.3 on 1 and 9 degrees of freedom, p value: 7.251e−06

In this other example relating to 3-octen-2-one, the critical probability is less than 0.05 and the Multiple $R^2$ is close to 1 (0.90). This compound is therefore significantly and strongly linked to the sensory classification.

In the end, 13 compounds were identified: heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2, and geranyl acetone.

The families of diunsaturated aldehydes, diunsaturated ketones, carboxylic acids and carboxylic acid derivatives are thus found to be represented here.

The value of the specific ions (by SPME GC/MS) of each of these 13 molecules is given in table 4 below.

TABLE 4

|  | (elution time) | |
|---|---|---|
|  | Retention time (min) | Specific ion (m/z) |
| 2,4-decadienal | 27.2 | 81 |
| 2,4-heptadienal | 19.6 | 81 |
| 2,4-nonadienal | 24.7 | 81 |
| 3,5-octadien-2-one | 20.2 | 95 |
| 3-octen-2-one | 17.3 | 111 |
| heptanal | 11.2 | 70 |
| 2-ethylhexanoic acid | 30.0 | 88 |
| heptanoic acid | 30.1 | 60 |
| hexanoic acid | 27.7 | 60 |
| geranyl acetone | 28.0 | 151 |
| myristate-1 | 31.8 | 228 |
| laurate-1 | 37.2 | 112 |
| myristate-2 | 41.1 | 228 |

Table 5 below presents the sums of the surface areas of the specific ion peaks by SPME/GC-MS of these 13 molecules for each of the 10 batches of microalgal flour compositions (relative value: 100% attributed to Ref batch 2).

TABLE 5

|  | Total surface areas of the specific ions of the 13 molecules (%) |
|---|---|
| Batch 111 | 1.4 |
| Batch 31 | 2.2 |
| Batch 21 | 6.3 |
| Batch 23 | 4.7 |
| Ref Batch 1 | 13.3 |
| Batch 131 | 15.2 |
| Batch 24 | 51.7 |
| Batch 53 | 64.3 |
| Batch 61 | 58.4 |
| Ref Batch 2 | 100 |

The olfactory thresholds in water, attributed to these 13 compounds, are presented in table 6 below.

TABLE 6

|  | olfactory threshold in water (ppb) |
|---|---|
| 2,4-decadienal | 0.07 |
| 2,4-heptadienal* | 0.1 |
| 2,4-nonadienal | 0.01 |
| 3,5-octadien-2-one* | 1 |
| 3-octen-2-one* | 1 |
| heptanal | 3 |
| 2-ethylhexanoic acid* | 1000 |
| heptanoic acid | 3000 |
| hexanoic acid | 3000 |
| geranyl acetone | 60 |
| myristate-1* | 1 |
| laurate-1* | 1 |
| myristate-2* | 1 |

*olfactory threshold established by the applicant company

Table 7 below presents the sum of the values of individual flavors of these 13 compounds, and therefore the total flavor value, determined from the relative contents of the 13 compounds and their olfactory thresholds (in the same way as the first approach):

FV total=ΣFVx(some of the individual FVs), with FVx=Concentration of the compound x/olfactory threshold of the compound x) for each of the 10 batches of microalgal flour compositions (value of 100% attributed to Ref batch 2).

TABLE 7

|  | Total flavor value (%) |
|---|---|
| Batch 111 | 0.92 |
| Batch 31 | 0.44 |
| Batch 21 | 0.52 |
| Batch 23 | 0.40 |
| Ref Batch 1 | 17.7 |
| Batch 131 | 24.33 |
| Batch 24 | 31.7 |
| Batch 53 | 57.3 |
| Batch 61 | 65.6 |
| Ref Batch 2 | 100 |

This analysis by GC/MS also makes it possible to consider the scale of following values:
batch 111>batch 31>batch 21>batch 23>reference batch 1>batch 131>batch 24>batch 53>batch 61>reference batch 2.

There is clearly a perfect correspondence between the scale of sensory analysis in food formation and that of the flavor values of the 13 molecules.

The microalgal flour compositions in accordance with the invention, in particular those having an optimized sensory profile, can therefore be defined by their relative content of 13 particular volatile organic compounds.

The invention claimed is:

1. A microalgal flour composition having a total content of 13 volatile organic compounds between 1% and 25% relative to that of a reference microalgal flour composition of unacceptable organoleptic quality, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone, and
when the microalgal flour composition is analyzed by SPME/GC-MS method A, the 13 volatile organic compounds have m/z ratios and retention times as follows:
2,4-decadienal: m/z of 81, retention time of approximately 27.2 min;
2,4-heptadienal: m/z of 81, retention time of approximately 19.6 min;
2,4-nonadienal: m/z of 81, retention time of approximately 24.7 min;
3,5-octadien-2-one: m/z of 95, retention time of approximately 20.2 min;
3-octen-2-one: m/z of 111, retention time of approximately 17.3 min;
heptanal: m/z of 70, retention time of approximately 11.2 min;
2-ethylhexanoic acid: m/z of 88, retention time of approximately 30.0 min;
heptanoic acid: m/z of 60, retention time of approximately 30.1 min;
hexanoic acid: m/z of 60, retention time of approximately 27.7 min;
geranyl acetone: m/z of 151, retention time of approximately 28.0 min;
myristate-1: m/z of 228, retention time of approximately 31.8 min;
laurate-1: m/z of 112, retention time of approximately 37.2 min; and
myristate-2: m/z of 228, retention time of approximately 41.1 min;
wherein the SPME/GC-MS method A comprises:
introducing a 3 gram sample of the microalgal flour composition to a sealed 20 mL SPME flask and incubating at 60° C. for 15 min to form an incubated 3 gram sample;
extracting the incubated 3 gram sample with divinylbenzene/carboxen/polydimethylsiloxane df 50/30 µm SPME fiber at 60° C. for 45 min to form an impregnated SPME fiber; and
subjecting the impregnated SPME fiber to GC-MS using a CPwax52 60 m×0.25 mm×0.25 µm column; helium gas at 1.5 mL/min; a temperature program of 50° C. isotherm for 3 min, increasing temperature 5° C./min until reaching 230° C., then isotherm at 230° C. for 20 min; and detecting by electron impact mass spectrometry.

2. The composition of claim 1, wherein the total surface area of the chromatography peaks after the SPME/GC corresponding to the 13 volatile organic compounds is between 1% and 25% relative to the reference microalgal flour composition of unacceptable organoleptic quality.

3. A composition for tasting a microalgal flour composition comprising:
5-10% of the microalgal flour composition of claim 1;
0.5-2% of sugar; and
0.1-0.5% of vanilla flavoring;
the remainder being skimmed milk,
the percentages being by weight of the composition.

4. The composition of claim 3, said composition comprising:
approximately 7% of microalgal flour composition;
approximately 0.25% of vanilla flavoring;
approximately 1% of sugar; and
the remainder being skimmed milk.

5. A method for preparing a composition for tasting a microalgal flour, comprising the homogenization of a composition of claim 3, and heating of the composition at 60-85° C. for 2-10 minutes.

6. The method of claim 5, said method comprising heating at approximately 75° C. for approximately 5 minutes.

7. A method for testing the organoleptic qualities of a microalgal flour, comprising preparing a composition according to the method of claim 5 and evaluating the organoleptic qualities by a panel of testers.

8. A method for evaluating the organoleptic quality of the microalgal flour composition of claim 1, the microalgal flour composition comprising volatile organic compounds, the method comprising;
construction of a first matrix associating microalgal flour compositions, including two controls of acceptable and unacceptable organoleptic quality, with the evaluation of their organoleptic qualities by a sensory panel of at least 10 individuals,
construction of a second matrix associating the microalgal flour composition with the presence of the volatile organic compound analysis profile, and
correlation of the first matrix with the second to produce a relationship model on the basis of which the compositions having an optimized organoleptic profile can thus be characterized by their analytical profile of volatile organic compounds.

9. The method of claim 8, wherein the sensory analysis descriptors comprise color, coating texture, sweetness, and the following flavors: mushroom, cereals, butter/dairy product, rancid oil and vegetable aftertaste.

10. The method of claim 8, wherein the sensory analysis is carried out using a composition prepared by homogenization and heating, at 60-85° C. for 2-10 minutes, the composition comprising:
5-10% of microalgal flour composition;
0.5-2% of sugar;
0.1-0.5% of vanilla flavoring; and
the remainder being skimmed milk,
the percentages being by weight of the composition.

11. The method of claim 8, wherein the analysis of the volatile organic compounds is carried out by SPME/GC or SPME/GC-MS.

12. The method of claim 8, wherein the volatile organic compounds belong to the families of saturated and diunsaturated aldehydes, unsaturated ketones and carboxylic acids and derivatives thereof.

13. A method of determining the organoleptic quality of the microalgal flour composition of claim 1, comprising determining the total content of 13 volatile organic compounds, the 13 volatile organic compounds being heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

14. The method of claim 13, wherein the total content of 13 volatile organic compounds is determined by SPME/CG.

15. The method of claim 13, wherein the total content of 13 volatile organic compounds is determined by SPME/GC-MS.

16. The method of claim 13, wherein a low total content of 13 volatile organic compounds is associated with an optimized organoleptic quality.

17. The method of claim 14, wherein the total content of the 13 volatile organic compounds is determined by the total surface area of the chromatography peaks after SPME/GC corresponding to the 13 volatile organic compounds.

18. The method of claim 13, wherein the total content of the 13 volatile organic compounds is compared to that of a reference microalgal flour composition or compositions for which the organoleptic qualities are defined as unacceptable or acceptable.

19. The method as claimed in claim 17, wherein the total surface area of the chromatography peaks corresponding to the 13 volatile compounds is compared to that of a reference microalgal flour composition or compositions for which the organoleptic qualities are defined as unacceptable or acceptable.

* * * * *

UNITED STATES PATENT AND TRADEMARK OFFICE
CERTIFICATE OF CORRECTION

PATENT NO. : 11,016,071 B2
APPLICATION NO. : 15/926899
DATED : May 25, 2021
INVENTOR(S) : Druon et al.

Page 1 of 1

It is certified that error appears in the above-identified patent and that said Letters Patent is hereby corrected as shown below:

On the Title Page

Item (72) Inventors: please replace "Marilynne Guillemant" with "Marilyne Guillemant".

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*